(12) United States Patent
Ando et al.

(10) Patent No.: US 8,329,858 B2
(45) Date of Patent: Dec. 11, 2012

(54) METHOD OF CONTROLLING OIL-ABSORBING PROPERTIES OF A SILICONE RUBBER POWDER

(75) Inventors: Kazuhiko Ando, Chiba (JP); Junichi Uchiyama, Chiba (JP)

(73) Assignee: Dow Corning Toray Co., Ltd., Tokyo (JP)

( * ) Notice: Subject to any disclaimer, the term of this patent is extended or adjusted under 35 U.S.C. 154(b) by 0 days.

(21) Appl. No.: 12/966,764

(22) Filed: Dec. 13, 2010

(65) Prior Publication Data

US 2011/0105627 A1 May 5, 2011

Related U.S. Application Data

(62) Division of application No. 12/093,856, filed as application No. PCT/JP2006/323521 on Nov. 17, 2006, now Pat. No. 7,875,699.

(30) Foreign Application Priority Data

Nov. 17, 2005 (JP) ................................. 2005-332428

(51) Int. Cl.
*C08F 6/00* (2006.01)

(52) U.S. Cl. ...... 528/503; 528/480; 528/491; 528/502 R; 528/10; 528/31; 524/261; 524/266; 524/268; 524/588; 524/858

(58) Field of Classification Search .................... 528/10, 528/30, 31, 32, 33, 34, 35, 36, 37, 38, 39, 528/40, 41, 42, 43, 480, 481, 502 R, 503; 524/261, 266, 267, 268, 588, 858; 424/69, 424/78.02, 78.03, 401, 486, 489, 497, 50
See application file for complete search history.

(56) References Cited

U.S. PATENT DOCUMENTS

| | | | |
|---|---|---|---|
| 4,594,134 A | 6/1986 | Hanada et al. | |
| 4,742,142 A | 5/1988 | Shimizu et al. | |
| 4,806,592 A | 2/1989 | Saruyama | |
| 5,756,568 A | 5/1998 | Morita et al. | |
| 6,025,435 A | * 2/2000 | Yamakawa et al. | 524/862 |
| 6,238,656 B1 | 5/2001 | Morita et al. | |

FOREIGN PATENT DOCUMENTS

| | | |
|---|---|---|
| EP | 0350519 A1 | 1/1990 |
| JP | 59068333 A | 4/1984 |
| JP | 62243621 A | 10/1987 |
| JP | 63077942 A | 4/1988 |
| JP | 63202658 A | 8/1988 |
| JP | 64070558 A | 3/1989 |
| WO | 2006/001458 A2 | 1/2006 |
| WO | 2006/040964 A1 | 4/2006 |
| WO | 2006/070903 A1 | 7/2006 |
| WO | 2006/135036 A1 | 12/2006 |
| WO | 2007/026727 A1 | 3/2007 |
| WO | 2007/055395 A1 | 5/2007 |

OTHER PUBLICATIONS

English language abstract for JP59068333 extracted from espacenet.com database, dated Jan. 19, 2009.
English language abstract for JP62243621 extracted from espacenet.com database, dated Oct. 24, 2008.
English language abstract for JP63077942 extracted from espacenet.com database, dated Jan. 19, 2009.
English language abstract for JP63202658 extracted from espacenet.com database, dated Jan. 19, 2009.
English language abstract for JP64070558 extracted from PAJ database, dated Jan. 19, 2009, 18 pages.
PCT International Search Report for PCT/JP2005/011864, dated Jan. 20, 2006, 5 pages.
PCT International Search Report for PCT/JP2005/018405, dated Mar. 22, 2006, 6 pages.
PCT International Search Report for PCT/JP2005/024196, dated Mar. 20, 2006, 3 pages.
PCT International Search Report for PCT/JP2006/312088; dated Sep. 22, 2006, 3 pages.
PCT International Search Report for PCT/JP2006/317033, dated Nov. 27, 2006, 3 pages.
PCT International Search Report for PCT/JP2006/322701, dated Feb. 15, 2007, 3 pages.
PCT International Search Report for PCT/JP2006/323521, dated Mar. 23, 2007, 3 pages.

* cited by examiner

*Primary Examiner* — Frances Tischler
(74) *Attorney, Agent, or Firm* — Howard & Howard Attorneys PLLC

(57) ABSTRACT

A method of controlling oil-absorbing properties of a silicone rubber powder characterized by keeping a silicone rubber powder in hot storage at a temperature in the range of 40° C. to 150° C. or in cold storage at a temperature in the range of 0° C. to 10° C.

9 Claims, No Drawings

METHOD OF CONTROLLING OIL-ABSORBING PROPERTIES OF A SILICONE RUBBER POWDER

CROSS REFERENCE TO RELATED APPLICATIONS

This application is a divisional of and claims priority to U.S. patent application Ser. No. 12/093,856, filed on May 15, 2008, now U.S. Pat. No. 7,875,699, hereby incorporated by reference in its entirety, which claims priority to and all the advantages of International Patent Application No. PCT/JP2006/323521, filed on Nov. 17, 2006, which claims priority to Japanese Patent Application No. JP 2005-332428, filed on Nov. 17, 2005 in Japan, which is hereby incorporated by reference in its entirety.

TECHNICAL FIELD

The present invention relates to a method of controlling oil-absorbing properties of a silicone rubber powder.

BACKGROUND ART

Silicone rubber powders are often mixed with cosmetic materials for improving feel of use. In cosmetic materials, silicone rubber powder is usually mixed with oiling agents, and stability of the oil-absorbing properties of such powder influences the stability of viscosity and feel of use of the cosmetic material.

A silicone rubber powder is prepared, e.g., by curing a liquid silicone rubber composition by dispersing the composition in water and then removing water (see Japanese Unexamined Patent Application Publication (hereinafter referred to as "Kokai") S62-243621 and Kokai S63-77942). After preparation, the silicone rubber powder is packaged and stored at room temperature prior to shipment, and during such storage, particles of the powder aggregate, and with a lapse of time increase their oil-absorbing properties. Although it would be desirable for the silicone rubber powder to have stable oil-absorbing properties directly after production, until the present time this objective could be achieved only after storing the silicone rubber powder for several months at room temperature prior to shipment.

It is an object of the present invention to provide a method for stabilization of oil-absorbing properties of a silicone powder suitable for use in cosmetic materials, especially for stabilization of the aforementioned properties in the aforementioned powder mixed with oil.

DISCLOSURE OF INVENTION

The above problem is solved by the present invention that provides a method of controlling oil-absorbing properties of a silicone rubber powder characterized by keeping a silicone rubber powder in hot storage at a temperature in the range of 40° C. to 150° C., or in cold storage at a temperature in the range of 0° C. to 10° C.

EFFECTS OF INVENTION

Effect of the method of the invention for controlling oil-absorbing properties of a silicone rubber powder consists of stabilizing the aforementioned properties of the silicone powder when the latter is compounded with oil, e.g., in the preparation of a cosmetic material.

DETAILED DESCRIPTION OF THE INVENTION

There are no special restrictions with regard to a silicone rubber powder to which the method of the invention can be applied. An average particle size of the powder is preferably in the range of 0.1 μm to 10 mm, more preferably in the range of 0.1 μm to 1 mm, especially preferably in the range of 0.1 μm to 500 μm. The shapes of the particles may be substantially spherical, regular spherical, elliptical, or irregular. Most preferable are particles having a substantially spherical or regular spherical shape.

There are no special restrictions with regard to a method that can be used for the preparation of the silicone rubber powder. For example, one method consists of spraying a liquid silicone rubber composition into hot air and thus curing the composition, wherein the composition comprises an organopolysiloxane having in one molecule at least two alkenyl groups, an organohydrogenpolysiloxane having at least two silicon-bonded hydrogen atoms in one molecule, and a platinum catalysts such as chloroplatinic acid, alcohol solution of chloroplatinic acid, a complex of a chloroplatinic acid and olefin, a complex of a chloroplatinic acid and alkenylsiloxane, platinum black, platinum on a silica carrier, or the like (see Kokai S59-68333). Another method consists of curing the aforementioned liquid silicone rubber composition by dispersing it in water (see Kokai S62-243621, Kokai S63-77942, Kokai S63-202658, and Kokai S64-70558). Most preferable from the viewpoint of efficient production of uniform spherical silicone rubber powder are methods based on curing the liquid silicone rubber composition in water. In order to stably disperse the silicone rubber composition in water in a finely particulate form, the composition may be compounded with one or several non-ionic, cationic, or anionic surface-active agents. Since such surface-active agents are then introduced into cosmetic materials, they have to be acceptable for such application. The content of the surface-active agents in the composition is preferably in the range of 0.1 to 20 parts by mass, more preferably in the range of 0.5 to 10 parts by mass per 100 parts by mass of the silicone rubber composition.

Dispersion of the liquid silicone rubber composition in water can be carried out with the use of a colloidal mill, homogenizer, propeller-type stirrer, Combimix-type mixer, ultrasonic stirrer, or another known emulsifier. Curing of the liquid silicone rubber composition in water produces a slurry of the silicone rubber powder. Curing can be carried out, e.g., by holding the product at room temperature, or by heating. The silicone rubber powder can be recovered from the slurry, e.g., by holding the slurry in an oven, drying the slurry with the use of a cold or hot air flow, drying the slurry under a reduced pressure, or adding alcohol or another volatile organic solvent to the aqueous slurry and thus replacing the water and drying the slurry.

When the silicone rubber powder is used as a raw cosmetic material and contains a non-crosslinking oil, this produces a softer touch by a finger and skin and improves makeup conditions. The silicone rubber powder containing oil can be prepared by various methods, e.g., first by mixing the silicone rubber composition with oil that does not participate in a curing reaction of the composition and then curing the composition in a state finely dispersed in water, or by adding oil to an aqueous suspension of the silicone rubber powder, stirring the mixture, and thus impregnating the silicone rubber powder with the oil. The first method is more preferable.

The aforementioned non-crosslinking oil may be one that can be merely contained in the silicone rubber powder and naturally oozes out from the powder, or one that can be extracted from the powder with the use of a solvent. Examples of such non-crosslinking oils are non-crosslinking silicone oils and non-crosslinking organic oils. The silicone oils may comprise those which do not participate in a curing reaction. Such oils may have a linear, partially-branched linear, cyclic, or branched molecular structure, of which the linear molecular structure is preferable. Examples of such silicone oils are the following: a dimethylpolysiloxane capped at both thmolecular terminals with trimethylsiloxy groups, a copolymer of a dimethylsiloxane and a methylphenylsiloxane capped at both molecular terminals with trimethylsiloxy groups, a copolymer of a dimethylsiloxane and methyl (3,3,3-trifluoropropyl) siloxane capped at both molecular terminals with trimethylsiloxy groups, or a similar non-reactive silicone oil. When the silicone rubber composition used for forming the silicone rubber powder already contains the aforementioned silicone oil, in addition to the aforementioned non-reactive silicone oils the composition may also contain other silicone oils that do not influence the curing reaction such as dimethylpolysiloxanes which are capped at both molecular terminals with trimethylsiloxy groups or dimethylpolysiloxanes which are partially substituted with alkyl groups, phenyl groups, or 3,3,3-trifluoropropyl groups, etc. If the curing reaction is a reaction of addition, then apart from the aforementioned non-reactive silicone oil the composition may also contain dimethylpolysiloxanes which are capped at both molecular terminals with trimethylsiloxy groups or dimethylpolysiloxanes which are partially substituted with alkyl groups, phenyl groups, or 3,3,3-trifluoropropyl groups, etc. Furthermore, the composition may contain some constituents that may exert influence on the curing reaction such as those that remain as an unreacted residue, e.g. silicone oils such as a dimethylpolysiloxane capped at both molecular terminals with dimethylvinylsiloxy groups, a copolymer of a methylvinylsiloxane and a dimethylsiloxane capped at both molecular terminals with trimethylsiloxy groups, a dimethylpolysiloxane capped at both molecular terminals with dimethylhydrogensiloxy groups, a copolymer of a methylhydrogensiloxane and a dimethylsiloxy capped at both molecular terminals with trimethylsiloxy groups, as well as the aforementioned polysiloxanes where a part of the methyl groups in addition to methyl groups is substituted with alkyl groups, phenyl groups, or 3,3,3-trifluoropropyl groups. If curing is carried out by means of a condensation reaction, in addition to the aforementioned non-reactive silicone oils, the composition may further contain such silicone oils as a polysiloxane where methyl groups are partially substituted with alkenyl groups. In order to provide the aforementioned properties of non-participation in the curing reaction, the composition may also contain, as an unreacted residue, such silicone oils as a dimethylpolysiloxane capped at both molecular terminals with silanol groups where methyl groups are partially substituted with alkyl groups, phenyl groups, or 3,3,3-trifluoropropyl groups. There are no special restrictions with regard to the type of the aforementioned oils when the cross-linked silicone powder is then impregnated with a silicone oil.

The non-crosslinking organic oils can be exemplified by liquid paraffin, isoparaffin, hexyl laurate, isopropyl myristate, myristyl myristate, cetyl myristate, 2-octyldodecyl myristate, isopropyl palmitate, 2-ethylhexyl palmitate, butyl stearate, decyl oleate, 2-octyldodecyl oleate, myristyl lactate, cetyl lactate, lanolin acetate, stearic alcohol, cetostearic alcohol, oleic alcohol, avocado oil, almond oil, olive oil, cacao oil, jojoba oil, sesame oil, safflower oil, soybean oil, camellia oil, squalane oil, persic oil, castor oil, mink oil, cotton seed oil, coconut oil, yolk oil, beef tallow, lard, polypropyleneglycol mono oleate, neopentylglycol-2-ethylhexanoate, or a similar glycolester oil; triglyceride isostearate, triglyceride of a palm oil fatty acid, or a similar polyhydric alcohol ester oil; polyoxyethylenelauryl ether, and polyoxypropylenecetyl ether, or a similar polyoxyalkylene ether oil.

The aforementioned non-crosslinking oils are liquid and should have viscosity not exceeding 100,000 mPa·s, preferably not exceeding 50,000 mPa·s, and most preferably, not exceeding 10,000 mPa·s at 25° C. If the viscosity exceeds the upper recommended limit of the above range, it will be difficult either to form a silicone rubber powder, or to impregnate the silicone rubber powder with oil. The silicone oils mentioned above are recommended because they possess affinity to silicone rubber powders.

An amount of non-crosslinking oil contained in the silicone rubber powder should not exceed 80 mass %, preferably should not exceed 50 mass %. The silicone rubber powder with the content of oil exceeding the above limit will be difficult to prepare, and the cosmetic product that contains such oil will become sticky.

According to the first embodiment of the invention, the silicone rubber powder is kept in hot storage at a temperature in the range of 40° C. to 150° C., preferably in the range of 40° C. to 100° C., and most preferably in the range of 40° C. to 80° C. In particular, it is recommended to store the silicone rubber powder in a packaged state. After storing with heating, the silicone rubber powder has to be cooled. Normally, if the silicone rubber powder is stored at room temperature (25° C.), oil-absorbing properties of the powder will change with time, and, therefore, it will be necessary to postpone the shipment until the oil-absorbing properties are stabilized. The method of the invention makes it possible to accelerate stabilization of oil-absorbing properties of the silicone powder and, thus, to shorten the time till shipment. Compounding of the obtained silicone rubber powder with a cosmetic material makes it possible to stabilize viscosity and feel of use of the latter. In accordance with the method of this embodiment, a silicone rubber powder with stabilized oil-absorbing properties can be obtained after keeping in hot storage for 1 to 2 days.

According to the second embodiment of the invention, the silicone rubber powder is kept in cold storage at a temperature in the range of 0° C. to 10° C. In particular, it is recommended to store the silicone rubber powder in a packaged state. Normally, if the silicone rubber powder is stored at room temperature (25° C.), oil-absorbing properties of the powder will change with time, and, therefore, it will be necessary to postpone the shipment until the oil-absorbing properties are stabilized. In contrast to this, the method of the invention is capable of suppressing changes in the oil-absorbing properties of the silicone rubber powder till the time of shipment and makes it possible to maintain the same oil-suppressing properties as those obtained directly after manufacture. Therefore, by compounding the obtained silicone rubber powder with a cosmetic material it becomes possible to stabilize viscosity and feel of use of the latter. In accordance with the method of this embodiment, the silicone rubber powder is kept in cold storage until it is ready for shipment, more specifically, until this powder is compounded with the oiling agent.

Thus, the silicone rubber powder prepared as described above is suitable for use as a cosmetic raw material. Cosmetic products related to the present invention may be prepared from the cosmetic raw materials mentioned above, as well as from other cosmetic raw materials. The cosmetic products themselves can be exemplified by soaps, body shampoos, facial creams or other washing-type cosmetics; toilet water, basic cosmetics such as cream-emulsions and packs; makeup cosmetics such as face powder, foundation, or similar base makeup cosmetics, cheek rouge, eye shadow, eye liner, mascara, or similar skin and eye cosmetics, manicure, etc.; shampoo, hair rinse, hair conditioner, hair-growth agent, hair growth stimulant, hair dying agent, or similar hair cosmetics; aromatics, eau de Cologne, or similar perfumes; tooth polishing substances; bath agents, hair-removing agents, lotions for shaving, perspiration inhibitors, deodorants, sunburn blockers, or other specific cosmetics. The aforementioned cosmetic products may exist in various forms, e.g., aqueous solutions, oil solutions, emulsions, creams, foams, semi-solid matters, solid matters, powders, etc. They also may be prepared as sprays.

The above-described cosmetic materials contain the cosmetic raw materials can be made from aqueous suspensions of the aforementioned silicone rubber powder in combination with other cosmetic raw materials which may be based on avocado oil, almond oil, olive oil, cacao oil, beef tallow, sesame oil, wheat embryo oil, safflower oil, shea butter, tartar oil, camellia oil, persic oil, castor oil, grape oil, macadamia nut oil, mink oil, egg yoke oil, Japan wax, coconut oil, rose hip oil, hardened oil, or similar oils and fats; orange roughy oil, carnauba wax, candellila wax, spermaceti oil, jojoba oil, montan wax, beeswax, lanolin, or similar waxes; liquid paraffin, Vaseline, ceresine, microcrystalline wax, squalane, or similar hydrocarbons; lauric acid, myristic acid, palmitic acid, stearic acid, oleic acid, behenic acid, undecylenic acid, oxystearic acid, linoleic acid, lanolic acid, synthetic fatty acids, or similar higher fatty acids; ethyl alcohol, isopropyl alcohol, lauric alcohol, cetylic alcohol, cetostearyc alcohol, stearic alcohol, behenic alcohol, lanolic alcohol, hydrogenated lanolic alcohol, hexyldecanol, octyldodecanol, isostearic alcohol, or similar alcohols; cholesterol, dihydrocholesterol, fitosterol, or similar sterols; ethyl linoleate, isopropyl myristate, isopropyl lanoleate, hexyl laurate, myristyl myristate, cetyl myristate, octyldodecyl myristate, decyl oleate, octyldodecyl oleate, hexyldecyl dimethyloctanate, cetyl octanate, cetyl palmitate, glycerol trimyristate, tri(capryl-caprylic acid) glycerol, propylene glycol dioleate, glycerol triisostearate, glycerol triisooctoate, cetyl lactate, myristyl lactate, diisostearyl maleate, or similar fatty acid esters; glycerol, propylene glycol, 1,3-butylene glycol, polyethylene glycol, sodium d, 1-pyrrolidoncarboxylate, sodium lactate, sorbitol, sodium hyalurate, or similar moisture-retaining agents; higher fatty acid soaps, a salt of a higher alcohol sulfuric acid ester, a salt of an N-acylglutamic acid, a salt of a phosphoric acid ester, or similar anionic surface-active agents, cationic surface-active agents, a betain-type, amino-type, imidazole-type, lethicine-type, other amphoteric-type surface-active agents, polyhydric-alcohol ester type, ethyl-oxide condensation-type, or similar non-ionic-type surface-active agents; pigments such as iron oxide or similar color pigments, zinc oxide, titanium oxide, zirconium oxide, or similar white-color pigments, mica, talc, sericite, or similar extender pigments; dimethylpolysiloxane, methylphenylpolysiloxane, octamethyltetracyclosiloxane, decamethylcyclopentasiloxane, polyether-modified silicone oil, amino-modified silicone oil, or other silicone oils; purified water; carrageenan, alginic acid, gum arabic, tragacanth gum, pectin, starch, xanthan gum, polyvinyl alcohol, polyvinyl pyrrolidone, sodium polyacrylate, polyethylene glycol, or other thickeners, as well as various ultraviolet ray absorbants, antibacterial agents, anti-perspiration agents, anti-inflammatory agents, antiseptic agents, aromatic agents, antioxidants, pH-adjusters, and propellants.

There are no special restrictions with regard to the methods used for manufacturing the cosmetic materials. For example, the cosmetic materials can be produced in a batch process or in a continuous process by using such equipment as a homomixer, paddle mixer, Henschel mixer, homo dispenser, colloidal mill, propeller-type stirrer, homogenizer, in-line type continuous-action emulsifier, ultrasonic emulsifier, or a vacuum-type kneader.

EXAMPLES

The method of the invention for controlling oil-absorbing properties of the silicone rubber powder will be further described in more detail with reference to application examples. In the following examples, all values of viscosities correspond to viscosities at 25° C. The oil-absorbing properties of the silicone rubber powders were measured by the method described below.

[Oil-Absorbing Properties]

Change of oil-absorbing properties of the silicone rubber powders with time was evaluated in terms of the maximum amount of the absorbed oil. More specifically, by using an instrument for measuring absorbed amounts (Model. S-410 produced by Asahisouken Co., Ltd.), 10 g of the silicone rubber powder stored under predetermined conditions were gradually added under stirring conditions to a decamethylcyclopentasiloxane, and then the maximum amount of oil (g/10 g) absorbed by the silicone rubber powder was determined as the amount of the added decamethylcyclopentasiloxane that corresponded to the maximum stirring torque of the mixture.

Reference Example 1

A liquid silicone rubber composition was prepared by uniformly mixing the following components at −10° C.: 96 parts by mass of a dimethylpolysiloxane capped at both molecular terminals with dimethylvinylsiloxy groups and having a viscosity of 400 mPa·s (the content of vinyl groups=0.5 mass %); 4.5 parts by mass of a methylhydrogenpolysiloxane capped at both molecular terminals with trimethylsiloxy groups and having a viscosity of 20 mPa·s (the content of silicon-bonded hydrogen atoms=1.5 mass %); 49.5 parts by mass of a dimethylpolysiloxane capped at both molecular terminals with trimethylsiloxy groups and having a viscosity of 100 mPa·s; and an isopropanol solution of a chloroplatinic acid (the content of metallic platinum in terms of mass units was 50 ppm per mass of the composition). The obtained liquid silicone rubber composition was quickly mixed at 25° C. with 300 parts by mass of a 1.5 mass % aqueous solution prepared from pure water and polyoxyethylene (9 mole added) lauryl ether. Following this, the obtained mixture was passed through a homogenizer at a rate of 300 kgf/cm$^2$, whereby a uniform aqueous dispersion of a liquid silicone rubber composition was obtained. The dispersion was cured by being held at quiescence for 24 hours at 35° C. to produce an aqueous slurry of a silicone rubber powder. The slurry was dried in a hot-air-flow dryer, water was removed, and a silicone rubber powder was obtained. All particles of the powder were spherical and had an average diameter of 6 μm.

Comparative Example 1

The silicone rubber powder obtained in Reference Example 1 was stored at 25° C. Change in the oil-absorbing characteristics of the powder with time is shown in Table 1.

Application Example 1

The silicone rubber powder obtained in Reference Example 1 was kept in hot storage at 40° C. Change in the oil-absorbing characteristics of the powder with time is shown in Table 1.

Application Example 2

The silicone rubber powder obtained in Reference Example 1 was kept in hot storage at 60° C. Change in the oil-absorbing characteristics of the powder with time is shown in Table 1.

Application Example 3

The silicone rubber powder obtained in Reference Example 1 was kept in cold storage at 5° C. Change in the oil-absorbing characteristics of the powder with time is shown in Table 1.

TABLE 1

| Property | | Example | | | |
|---|---|---|---|---|---|
| | | Appl. Ex. 1 | Appl. Ex. 2 | Appl. Ex. 3 | Comp. Ex. 1 |
| Change of oil-absorbing property with time | | 40° C. | 60° C. | 5° C. | 25° C. |
| Maximum amount of absorbed oil (g/10 g) | after 1 day | 15 | 20 | 12 | 12.5 |
| | after 2 days | 20 | 23 | 14 | 14 |
| | after 3 days | 18 | 23 | 14 | 13 |
| | after 4 days | 18 | 22 | — | — |
| | after 5 days | 18 | 23 | — | — |
| | after 6 days | 20.5 | 24 | — | — |
| | after 7 days | 19 | 22 | 14 | 13.5 |
| | after 8 days | 20 | 23 | — | — |
| | after 11 days | 20 | 26 | 14 | 14 |
| | after 35 days | — | — | 14 | 17.5 |
| | after 77 days | — | — | 16 | 19 |
| | after 126 days | — | — | 17 | 23 |
| | after 184 days | — | — | 19 | 22.5 |
| | after 267 days | — | — | 22.5 | 25 |
| | after 329 days | — | — | 20 | 26 |
| | after 393 days | — | — | 19 | 23 |
| | after 479 days | — | — | 21 | 28 |

INDUSTRIAL APPLICABILITY

Since the method of the invention stabilizes oil-absorbing properties of a silicone rubber powder, the obtained silicone rubber powder can be used for cosmetic materials such as skin cosmetics, hair cosmetics, or other cosmetic products.

The invention claimed is:

1. A method of controlling the ability of a silicone rubber powder to absorb oil characterized by keeping the silicone rubber powder in cold storage at a temperature in the range of 5° C. to 10° C. for more than 35 days.

2. The method of claim 1, wherein said silicone rubber powder contains oil.

3. The method of claim 1, wherein said silicone rubber powder has an average particle size in the range of 0.1 µm to 10 mm.

4. The method of claim 1, wherein said silicone rubber powder has an average particle size in the range of 0.1 µm to 1 mm.

5. The method of claim 2, wherein said oil is a non-crosslinking silicone oil having a viscosity which does not exceed 100,000 mPa·s.

6. The method of claim 2, wherein said oil is a non-crosslinking silicone oil having a viscosity which does not exceed 50,000 mPa·s.

7. The method of claim 2, wherein said oil is a non-crosslinking organic oil having a viscosity which does not exceed 100,000 mPa·s.

8. The method of claim 2, wherein said oil is a non-crosslinking organic oil having a viscosity which does not exceed 50,000 mPa·s.

9. The method of claim 1, wherein the temperature is 5° C.

* * * * *